(12) United States Patent
Nakatani et al.

(10) Patent No.: US 12,357,614 B2
(45) Date of Patent: Jul. 15, 2025

(54) L-ERGOTHIONEINE-CONTAINING COMPOSITION

(71) Applicant: NAGASE & CO., LTD., Osaka (JP)

(72) Inventors: Takeshi Nakatani, Hyogo (JP); Nanami Nakashima, Hyogo (JP)

(73) Assignee: NAGASE & CO., LTD., Osaka (JP)

( * ) Notice: Subject to any disclaimer, the term of this patent is extended or adjusted under 35 U.S.C. 154(b) by 568 days.

(21) Appl. No.: 17/905,626

(22) PCT Filed: Mar. 4, 2021

(86) PCT No.: PCT/JP2021/008388
§ 371 (c)(1),
(2) Date: Sep. 2, 2022

(87) PCT Pub. No.: WO2021/177397
PCT Pub. Date: Sep. 10, 2021

(65) Prior Publication Data
US 2023/0126387 A1 Apr. 27, 2023

(30) Foreign Application Priority Data
Mar. 4, 2020 (JP) .............................. 2020-036577

(51) Int. Cl.
*C07D 233/84* (2006.01)
*A61K 31/417* (2006.01)
*A61K 31/4172* (2006.01)

(52) U.S. Cl.
CPC .............................. *A61K 31/4172* (2013.01)

(58) Field of Classification Search
CPC ............... C07D 233/84; A61K 31/417; A61K 31/4172; A61K 2300/00
See application file for complete search history.

(56) References Cited

U.S. PATENT DOCUMENTS

2020/0385769 A1   12/2020   Nakatani et al.

FOREIGN PATENT DOCUMENTS

| AU | 2013234815 A1 | 10/2019 |
| JP | 2009-126863 A | 6/2009 |
| JP | 2013-506705 A | 2/2013 |
| JP | 2019-149972 | 9/2019 |
| WO | WO2009045413 A1 | 9/2009 |
| WO | WO 2019/089878 A1 | 8/2019 |
| WO | WO 2019/163767 A1 | 8/2019 |

OTHER PUBLICATIONS

Erdelmeier et al., Cysteine as a Sustainable Sulfur Reagent for the Protecting-Group-Free Synthesis of Sulfur-Containing Amino Acids: Biomimetic Synthesis of L-ergothioneine in Water, Green Chemistry, vol. 14, No. 8, pp. 2256-2265 (Year: 2012).*
Office Action issued in the corresponding Chinese Patent Application No. 202180018596.6, dated Dec. 2, 2024.
Office Action issued in corresponding Chinese Patent Application No. 202180018596.6, dated Mar. 28, 2025, in 10 pages.
Rejection Decision issued in corresponding Tawainese Patent Application No. 110107636, dated Mar. 10, 2025, in 9 pages.
International Preliminary Report on Patentability (IB338) issued in application No. PCT/JP2021/008388, dated Sep. 15, 2022.
Office Action issued in corresponding Japanese Patent Application No. 2022-504452, dated Feb. 28, 2025, in 8 pages.
Office Action issued in corresponding Brazilian Application No. BR112022017415-2 dated Aug. 14, 2023.
International Search Report and Written Opinion issued in application No. PCT/JP2021/008388, dated Sep. 1, 2021.
Extended Search Report issued in the corresponding European Patent Application No. 21764176.0, dated Mar. 1, 2024.
S. Yoshida et al., Apr. 4, 2019, Anti-oxidative Amino Acid L-ergothioneine Modulates the Tumor Microenvironment to Facilitate Adjuvant Vaccine Immunotherapy, Front. Immunol. 10(671).
S. Yoshida et al., Jan. 23, 2017, The Anti-Oxidant Ergothioneine Augments the Immunomodulatory Function of TLR Agonists by Direct Action on Macrophages, PLoS One 12(1):e0169360.
Bulletin of the College of Agriculture, Tamagawa University 1: 17-41 (2016).
Office Action dated Dec. 1, 2020 in Japanese Application No. 2020-036577.
Office Action issued in the corresponding Taiwanese Patent Application No. 110107636, dated Nov. 5, 2024.
Office Action issued in the corresponding Chinese Patent Application No. 202180018596.6, dated Nov. 5, 2024.

* cited by examiner

*Primary Examiner* — Brenda L Coleman
(74) *Attorney, Agent, or Firm* — KNOBBE, MARTENS, OLSON & BEAR, LLP (57) ABSTRACT

In a composition in which L-ergothioneine (EGT) and N,N-dimethyl-L-2-thiohistidine (DTH), it makes possible to suppress coloring of the composition. A composition comprising EGT and DTH is prepared in which the content of DTH is reduced.

8 Claims, 4 Drawing Sheets

L-ERGOTHIONEINE-CONTAINING COMPOSITION

TECHNICAL FIELD

The present invention relates to an L-ergothioneine (EGT)-comprising composition. More specifically, the present invention relates to a composition in which stability of L-ergothioneine (EGT) is enhanced in the presence of N,N-dimethyl-L-2-thiohistidine (DTH), and a method for producing the same.

BACKGROUND ART

L-ergothioneine (herein, sometimes referred to as "EGT"), a kind of sulfur-containing amino acid, is known to have various physiological activities including an antioxidant ability.

For example, Non-Patent Document 1 discloses that EGT has a function of improving the effect of immunotherapy by a cancer vaccine including a tumor-associated antigen (TAA) and an adjuvant. Patent Document 1 discloses that EGT has a function of treating bacterial infections. In Experiment 1 of Patent Document 1, it has been confirmed that EGT at 5 mM and 50 mM suppresses the growth of *Escherichia coli*. Therefore, it can be understood that the suppression of bacterial infections described in Patent Document 1 is achieved by direct suppression of the growth of bacteria by EGT.

Non-Patent Document 2 discloses that the production of cytokines (IL-6, IL-12p40, IL-1β, IL-10) by mouse bone marrow-derived macrophages under stimulation conditions with a toll-like receptor ligand is promoted by 10 mM EGT and not by 1 mM EGT, and that in the co-culture of F4/80 macrophages and OT-II CD4+ T cells, Th17 polarization of OT-II CD4+ T cells is promoted by 30 mM EGT. As described above, Non-Patent Document 2 discloses that EGT at a high concentration of 10 mM or more activates macrophages.

Non-Patent Document 3 is a review of the physiological activities of EGT. Non-Patent Document 3 discloses that EGT is absorbed and accumulated in the bodies of animals and plants.

PRIOR ART DOCUMENTS

Patent Document

Patent Document 1: WO2019/089878

Non-Patent Document

Non-Patent Document 1: S. Yoshida et al., Front. Immunol. 10:671(2019)
Non-Patent Document 2: PLoS ONE 12(1):e0169360
Non-Patent Document 3: Bulletin of the College of Agriculture, Tamagawa University 1: 17-41 (2016)

SUMMARY OF THE INVENTION

Problems to be Solved by the Invention

However, the formulation stability in compositions comprising EGT has not yet been thoroughly investigated. In particular, the influence of other coexisting components in compositions comprising EGT has not been reported in detail.

Means for Solving the Problems

In view of the above problems, as a result of intensive studies, it has been found that in a case of an EGT-comprising composition in which N,N-dimethyl-L-2-thiohistidine (DTH) coexists, EGT is destabilized, and accordingly, coloring of the EGT-comprising composition occurs, which has not been reported so far.

In order to solve this novel problem, the present inventors have found that in a composition comprising EGT and DTH, reducing the content of the DTH can enhance the stability of the EGT and suppress coloring of the composition, thereby completing the present invention.

That is, the present invention provides the following composition.

[1]
A composition comprising L-ergothioneine and N,N-dimethyl-L-2-thiohistidine,
  wherein a content of the N,N-dimethyl-L-2-thiohistidine is reduced.

[2]
The composition according to [1], wherein the content of the N,N-dimethyl-L-2-thiohistidine is reduced so that coloring of the composition is suppressed.

[3]
The composition according to [1] or [2], wherein the content of the N,N-dimethyl-L-2-thiohistidine is 50 parts by mass or less with respect to 100 parts by mass of the L-ergothioneine.

[4]
The composition according to any one of [1] to [3], wherein the content of the N,N-dimethyl-L-2-thiohistidine is 0.0001 parts by mass or more with respect to 100 parts by mass of the L-ergothioneine.

[5]
The composition according to any one of [1] to [4], wherein the content of the N,N-dimethyl-L-2-thiohistidine is 0.05 parts by mass or more with respect to 100 parts by mass of the L-ergothioneine.

[6]
A composition comprising L-ergothioneine and N,N-dimethyl-L-2-thiohistidine, wherein
  a content of the N,N-dimethyl-L-2-thiohistidine is 50 parts by mass or less with respect to 100 parts by mass of the L-ergothioneine for suppressing coloring of the composition.

The present invention also relates to the following production method.

[7]
A method for producing a composition comprising L-ergothioneine and N,N-dimethyl-L-2-thiohistidine and having suppressed coloring,
  the method including a step of reducing a content of the N,N-dimethyl-L-2-thiohistidine.

The present invention also relates to the following method.

[8]
A method for imparting a coloring-suppressing effect to a composition comprising L-ergothioneine and N,N-dimethyl-L-2-thiohistidine,
  wherein a content of the N,N-dimethyl-L-2-thiohistidine is 50 parts by mass or less with respect to 100 parts by mass of the L-ergothioneine.

Effect of the Invention

DTH has been found as a component that affects the stability of EGT. Accordingly, in a composition in which EGT and DTH coexist, reducing the content of DTH can enhance the formulation stability and suppress coloring of the composition.

DETAILED DESCRIPTION

The composition of the present invention is a composition comprising L-ergothioneine (EGT) and N,N-dimethyl-L-2-thiohistidine (DTH), in which the content of DTH is reduced.

[L-ergothioneine (EGT)]

EGT is a histidine derivative (N,N,N-trimethyl-L-2-thiohistidine), whose structure is represented by the following formula 1.

[Formula 1]

(1)

EGT can be obtained by a publicly known method such as a synthesis method, an extraction method, or a fermentation method, and also a commercially available product can be obtained and used.

Examples of the commercially available product of EGT include L-ergothioneine (manufactured by Tetrahedron).

N,N-dimethyl-L-2-thiohistidine (DTH)

DTH is an analog of EGT, whose structure is represented by the following formula 2.

[Formula 2]

(2)

DTH can be obtained by a publicly known method such as a synthesis method, an extraction method, or a fermentation method, and also a commercially available product can be obtained and used.

Examples of the commercially available product of DTH include N,N-dimethyl-L-2-thiohistidine (manufactured by Tetrahedron).

The EGT and/or DTH may be in the form of a free form or in the form of a salt. The salt of EGT and/or DTH may be a salt formed with a carboxyl group in these structures, or may be a salt formed with a trimethylamino group or a dimethylamino group. The L-ergothioneine or the L-ergothioneine analog may also be a solvate such as a hydrate.

The salt of EGT and/or DTH is not particularly limited as long as the salt is a pharmacologically or physiologically acceptable salt, and specific examples thereof include an organic acid salt, an inorganic acid salt, a salt with an organic base, and a salt with an inorganic base. Examples of the organic acid salt include monocarboxylates such as acetate, trifluoroacetate, butyrate, palmitate, and stearate; polyvalent carboxylates such as fumarate, maleate, succinate, and malonate; oxycarboxylates such as lactate, tartrate, and citrate; and organic sulfonates such as methanesulfonate, toluenesulfonate, and tosylate. Examples of the inorganic acid salt include hydrochloride, sulfate, nitrate, hydrobromide, and phosphate. Examples of the salt with an organic base include salts with organic amines such as methylamine, triethylamine, triethanolamine, diethanolamine, morpholine, piperazine, pyrrolidine, and ethylenediamine. Examples of the salt with an inorganic base include various salts such as salts with alkali metals such as sodium and potassium, alkaline earth metals such as calcium and magnesium, and metals such as aluminum. These salts of EGT and/or DTH may be used alone, or may be used in any combination of two or more thereof. The "pharmaceutically or physiologically acceptable salt" may include a solvate or hydrate of a salt.

In the following Examples, the present inventors have found that in a case of an EGT-comprising composition in which DTH coexists, EGT is destabilized, and accordingly, coloring of the EGT-comprising composition occurs, which has not been reported so far. Furthermore, the present inventors have found that in a composition comprising EGT and DTH, reducing the content of the DTH can enhance the stability of the EGT and suppress coloring of the composition. Aspects of the EGT-comprising composition in which DTH coexists are not particularly limited. For example, DTH may be added to the EGT-comprising composition, or may be endogenously comprised as, for example, an impurity in an extraction method, or a by-product in a synthesis method, a fermentation method, or the like.

In the composition of the present invention, "coloring is suppressed" means that the absorbance at 400 nm is reduced by reducing the content of DTH from a composition comprising EGT and DTH in equal amounts under the same pH condition. The reduction in absorbance at 400 nm can be determined using a publicly known spectrophotometer. For example, the reduction in absorbance at 400 nm is preferably at least a 5% reduction, more preferably at least a 10% reduction relative to a composition comprising EGT and DTH in equal amounts.

In the composition of the present invention, as to the content ratio of DTH to EGT, the content of DTH is preferably 50 parts by mass or less, more preferably 40 parts by mass or less, still more preferably 30 parts by mass or less, particularly preferably 20 parts by mass or less, most preferably 10 parts by mass or less with respect to 100 parts by mass of EGT, from the viewpoint of suppressing coloring of the composition and the viewpoint of the stability of EGT.

In addition, in the composition of the present invention, as to the content ratio of DTH to EGT, the content of DTH is preferably 0.0001 parts by mass or more, more preferably 0.001 parts by mass or more, still more preferably 0.005 parts by mass or more, particularly preferably 0.01 parts by mass or more, most preferably 0.05 parts by mass or more with respect to 100 parts by mass of EGT, from the viewpoint of the production efficiency of the composition and the like.

In addition, in the composition of the present invention, as to the content ratio of DTH to EGT, the content of DTH is preferably 0.0001 to 50 parts by mass, more preferably 0.001 to 40 parts by mass, still more preferably 0.005 to 30 parts by mass, particularly preferably 0.01 to 20 parts by mass, most preferably 0.05 to 10 parts by mass with respect to 100 parts by mass of EGT, from the viewpoint of suppressing coloring of the composition, the viewpoint of the stability of EGT, the viewpoint of the production efficiency of the composition, and the like.

In addition, in the composition of the present invention, the content of EGT is appropriately adjusted depending on the form and use of the formulation, the type and content of other components, and the like, and is not limited, but can be, for example, 0.000001 mass % or more with respect to the total amount of the composition, including 0.000005 mass % or more, 0.00001 mass % or more, 0.00005 mass % or more, 0.0001 mass % or more, 0.0005 mass % or more, and 0.001 mass % or more. In addition, the content of EGT can be, for example, 99.999 mass % or less with respect to the total amount of the composition, including 99.9 mass % or less, 99.5 mass % or less, 99 mass % or less, 98.5 mass % or less, and 98 mass % or less. In another embodiment, when prepared as a liquid formulation, the content of EGT is not limited, but can be, for example, 80 mass % or less with respect to the total amount of the composition, including 70 mass % or less, 60 mass % or less, 50 mass % or less, 40 mass % or less, 30 mass % or less, 20 mass % or less, 10 mass % or less, 5 mass % or less, and 1 mass % or less.

[Use]

In a composition comprising EGT and DTH, reducing the content of the DTH can enhance the stability of the EGT, and thus the present invention can be used to suppress coloring of the composition.

In addition, as described above, it is known that EGT has various physiological activities including antioxidant ability. Also in a composition comprising EGT and DTH, when using the present invention, the stability of EGT can be enhanced and its decomposition can be suppressed so that the EGT does not impair but can exhibit the inherent physiological activities.

Also in a composition comprising EGT and DTH, when using the present invention, the composition can be suitably used for antioxidation, for improving brain function, for anti-aging, for eye diseases, for whitening, for absorbing ultraviolet rays, for suppressing melanin production, for eliminating active oxygen species, for inhibiting elastase activity, for suppressing wrinkle formation, for suppressing skin sagging, for suppressing formation of skin spots, for suppressing dark rings around eyes, for reducing skin damage (suppressing photoaging) by ultraviolet rays, for dry skin, for sensitive skin, for improving hair, for promoting autophagy, and the like, which are the inherent physiological activities of EGT.

The composition of the present invention can further appropriately contain an active component or an additive that can be used for foods or drinks, foods with functional claims, foods for specified health uses, quasi-drugs, pharmaceutical products, cosmetic products, daily necessities, feeds, and the like, and can be appropriately formulated by a publicly known formulation method used for these items.

As cosmetic products and daily necessities, for example, the composition of the present invention can be formulated into a skin lotion, an emulsion, a gel, a serum, a cream, a sunscreen cream, a pack, a mask, a foundation, a face powder, a bathing agent, a body lotion, a shampoo, a rinse, a hair treatment, a hair conditioner, a hairdressing, a hair tonic, a toothpowder, a mouthwash, and the like.

[Formulation]

The composition of the present invention can be administered orally or parenterally (including externally) as, for example, a solid formulation such as a tablet, a capsule, a granule, or a powder; or as a liquid formulation such as a solution, a syrup, an injection, a cream, a lotion, a paste, an ointment, an emulsion (an oil-in-water emulsion, a water-in-oil emulsion, a multiple emulsion, a micro-emulsion, a PET-emulsion, a pickering emulsion), a gel (a hydrogel, an alcohol gel), or a suspension. For the solid formulation, an excipient, a lubricant, a binder, and a disintegrant can be used; and for the liquid formulation, a solvent, a solubilizing agent, an emulsifier, an emulsion stabilizer, a thickener, a humectant, a suspending agent, an tonicity agent, a buffering agent, an analgesic agent, and the like can be used. If necessary, an additive such as an antiseptic, an antioxidant, a colorant, a sweetener, or a perfume can also be used.

Examples of the excipient include sugar alcohols such as sorbitol, mannitol, and xylitol, saccharides such as glucose, white sugar, lactose, and fructose, crystalline cellulose, carmellose sodium, croscarmellose sodium, calcium hydrogen phosphate, wheat starch, rice starch, corn starch, potato starch, dextrin, β-cyclodextrin, light anhydrous silicic acid, titanium oxide, magnesium aluminate metasilicate, talc, kaolin, and olive oil.

Examples of the binder include cellulose derivatives such as methyl cellulose, ethyl cellulose, hydroxypropyl cellulose, and hydroxypropyl methyl cellulose, polyvinyl pyrrolidone, polyvinyl alcohol, acrylic acid-based polymers, gelatin, gum arabic, pullulan, pregelatinized starch, agar, tragacanth, sodium alginate, and propylene glycol alginate.

Examples of the disintegrant include starch, low-substituted hydroxypropyl cellulose, carboxymethyl cellulose calcium, croscarmellose sodium, hydroxypropyl starch, and partially pregelatinized starch.

Examples of the solvent include water, alcohol, propylene glycol, macrogol, sesame oil, and corn oil.

Examples of the lubricant include stearic acid, magnesium stearate, calcium stearate, polyoxyl stearate, cetanol, talc, hardened oil, sucrose fatty acid ester, dimethylpolysiloxane, beeswax, and white beeswax.

Examples of the solubilizing agent include polyethylene glycol, propylene glycol, mannitol, benzyl benzoate, ethanol, tris(hydroxymethyl)aminomethane, cholesterol, triethanolamine, sodium carbonate, and sodium citrate.

Examples of the suspending agent/emulsifier include surfactants such as stearylamine, triethanolamine, sodium lauryl sulfate, laurylaminopropionic acid, lecithin, benzalkonium chloride, benzethonium chloride, and glyceryl monostearate; hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose; and waxes such as shellac wax, beeswax, carnauba wax, spermaceti wax, lanolin, liquid lanolin, reduced lanolin, hard lanolin, cyclic lanolin, lanolin wax, candelilla wax, Japan wax, montan wax, and rice wax.

Examples of the tonicity agent include sodium chloride, glycerin, and D-mannitol.

Examples of the buffering agent include phosphate, acetate, carbonate, and citrate buffers.

Examples of the antiseptic include paraoxybenzoic acid esters, chlorobutanol, benzyl alcohol, phenethyl alcohol, dehydroacetic acid, and sorbic acid.

Examples of the antioxidant include sulfite and ascorbic acid.

When the composition of the present invention is formed into a solid formulation, a production method publicly known in the art can be used. Examples of the method include a method in which a product extruded, granulated, and molded by kneading a composition and passing the kneaded composition through a screen is pulverized and sized, and a method in which stirring granulation is performed by adding kneading water to the composition, followed by molding using a vertical granulator, and subsequently the granulated product is pulverized with a comil, and sieved. In addition, a method is included in which the formulation composition is compressed with a roller compactor, then pulverized with a roll granulator, and sieved. Furthermore, a method is included in which fluidized bed drying is performed after stirring granulation. Moreover, for example, in the case of producing by direct compression, a blended composition may be directly put into a tablet pressing machine and compressed.

[Food and Drink]

The composition of the present invention can also be used as a food and drink composition, or can be provided in a state of being comprised in foods or functional foods. Examples of such foods or functional foods include rice; various noodles including buckwheat noodles, Japanese wheat noodles, harusame noodles, Chinese noodles, instant noodles, and cup noodles; drinks such as soft drink, carbonated drink, nutritional drink, fruit drink, lactic acid drink, and sport drink; curry roux, stews, and various soups; frozen confectionery such as ice cream, ice sherbet, and shaved ice; confectionery such as Japanese candies, cookies, candies, gums, chocolates, tablet confectionery, snack confectionery, biscuits, jellies, jams, creams, and other baked confectionery; fish and livestock processed foods such as kamaboko, hanpen, hams, and sausages; dairy products such as processed milk and fermented milk; oils and fats, and oil-and-fat processed foods such as salad oil, tempura oil, margarine, mayonnaise, shortening, whipped cream, and dressing; condiments such as sauce, dressing, miso, soy sauce, and gravy; soups, stews, salads, side dishes, furikake, and pickled vegetables; and various other forms of health and nutrition supplements, foods with functional claims, and foods for specified health uses.

In addition, supplements (such as powders, granules, soft capsules, hard capsules, tablets, chewable tablets, fast dissolving tablets, syrups, and liquid formulations) comprising the composition of the present invention may be prepared.

The composition of the present invention can also be comprised in feeds for animals such as pets.

If necessary, additives are added to foods or drinks. Examples of such additives include glucose, fructose, sucrose, maltose, sorbitol, trehalose, stevioside, rubusoside, corn syrup, lactose, mannitol, dextrin, citric acid, sodium citrate, tartaric acid, malic acid, succinic acid, lactic acid, L-ascorbic acid, tocopherol, sodium erythorbate, glycerin, propylene glycol, glycerin fatty acid esters, polyglycerin fatty acid esters, sucrose fatty acid esters, sorbitan fatty acid esters, gum arabic, carrageenan, casein, gelatin, pectin, agar, vitamins B, nicotinic acid amide, calcium pantothenate, amino acids, calcium salts, surfactants, dyes, flavors, and preservatives.

The composition of the present invention can be used for foods or drinks for which indication of improvement, prevention, progress or the like of various symptoms or conditions is permitted. Here, in the present invention, foods or drinks for which indication of improvement, prevention, progress, or the like of symptoms or conditions is permitted are foods and drinks having an efficacy permitted/designated by the government or a public organization, and are, for example, foods with functional claims, health functional foods such as foods for specified health uses, and food and special-use foods. Note that the names and regulations of such foods and drinks vary depending on the situation, the times, and the system in each country, but those that are essentially the same are included in the present invention.

In the present invention, the blending amount of the composition of the present invention is not particularly limited, and is appropriately set depending on the purpose of application (target disease, type of symptom, etc.), applied target site, sex and age of the applied subject, product forms such as foods and drinks, foods with functional claims, foods for specified health uses, quasi-drugs, pharmaceuticals, cosmetics, daily necessities, or feeds, the method and number of administration or ingestion of them, and preference.

When the composition of the present invention is used, it is possible to set an effective amount that can exhibit the inherent physiological activities of EGT as an ingesting amount (applied amount) per day. For example, when ingested by (applied to) a healthy adult, the ingesting amount (applied amount) of EGT per day can be used at, for example, 0.005 to 4,000 mg, preferably 0.1 to 3,000 mg, more preferably 0.5 to 2,000 mg, still more preferably 1 to 1,000 mg, particularly preferably 2 to 500 mg, most preferably 3 to 300 mg.

When the composition of the present invention is used as foods or drinks, the foods or drinks are not limited, but preferably functional foods from the viewpoint of being able to display the inherent physiological activities of EGT. Among the functional food products, foods with functional claims, nutritive functional foods, nutrition supplements, and foods for specified health uses are exemplified. Among them, foods with functional claims are preferable from the viewpoint of being able to clearly display the use.

[Applied Subject]

A subject to which the composition of the present invention is applied is not particularly limited as long as the subject is in the age group requiring the inherent physiological activities of EGT, but the subject may be around 30 years old or older, which is in an age group that is likely to receive stress from living environment such as work, may be a middle-aged person (around 45 years old or older and under 55 years old) who is in an age group that is likely to feel a change in the body due to a change in hormone balance, a change in living environment, or the like, or may be an aged person (55 years old or older).

[pH]

The pH of the composition of the present invention is appropriately set depending on the type and content of other blending components, the formulation form, the method of use, and the like, and is not limited as long as the pH is within a pharmaceutically or physiologically acceptable range, but can be, for example, pH 2 to 10. From the viewpoint of stably exhibiting the effect of the present invention, the pH of the composition of the present invention can be, for example, pH 2 to 10, pH 2 to 9, pH 2 to 8, pH 2 to 7, pH 3 to 10, pH 3 to 9, pH 3 to 8, pH 3 to 7, pH 4 to 10, pH 4 to 9, pH 4 to 8, pH 4 to 7, pH 5 to 10, pH 5 to 9, pH 5 to 8, pH 5 to 7, pH 6 to 10, pH 6 to 9, pH 6 to 8, or pH 6 to 7.

[Method for Producing Composition Comprising EGT and DTH and Having Suppressed Coloring]

In the present invention, the method for producing a composition comprising EGT and DTH and having suppressed coloring includes a step of reducing the content of DTH.

As the step of reducing the content of DTH, any publicly known means can be utilized as long as the DTH content is reduced. For example, when EGT and DTH are mixed to prepare a composition, a step of reducing the content ratio of DTH to EGT can be adopted. As described above, the mode in which DTH coexists in an EGT-comprising composition is not particularly limited, and may be, for example, a mode in which DTH exists in impurities in an EGT extraction method, or a mode in which DTH exists as a by-product in a synthesis method, a fermentation method, or the like.

Examples of the method for reducing DTH in impurities in a method for extracting EGT from mushrooms, plants, and the like include solvent extraction, separation by the solubility difference, chromatography such as chromatography using an adsorbent such as silica gel or alumina, cation exchange chromatography, anion exchange chromatography, hydrophobic chromatography, gel filtration chromatography, thiopropyl-sepharose 6B chromatography, or reverse phase chromatography, methods such as crystallization, activated carbon treatment, and membrane treatment, and methods combining these methods.

As a method for producing EGT by a fermentation method, a method using *E. coli* or the like is publicly known from WO 2019/163767 A and the like. Examples of the method for reducing DTH in impurities in a fermentation method for EGT include methods described in Examples described below. Specifically, in the fermentation method for EGT, adopting the step of deleting the metJ gene of bacteria belonging to Enterobacteriaceae having EGT production ability can reduce DTH in a culture solution, and efficiently produce EGT.

As the step of deleting the metJ gene, a publicly known method can be used, and examples thereof include a method for knocking out or knocking down the metJ gene by homologous recombination, mutation treatment, genome editing, or the like.

Examples of the bacteria belonging to Enterobacteriaceae having EGT production ability include, but are not limited to, bacteria belonging to the genera *Escherichia*, *Enterobacter*, *Pantoea*, *Klebsiella*, and *Salmonella*. Particularly preferable examples of the enterobacteria include enterobacteria of *Escherichia* such as *Escherichia coli* and *Pantoea* such as *Pantoea ananatis*.

The culture of bacteria belonging to Enterobacteriaceae can be performed by a standard method. Specifically, an LB medium, a 2×YT medium, an NZY medium, an M9 medium, an SOC medium, a YPD medium, or the like can be used. The medium described above can be used to produce EGT and DTH, but the medium to be used is not limited thereto. The produced EGT and DTH may be accumulated in the bacterial cells, or may be secreted and accumulated outside the cells (in the culture solution).

The collection of EGT and DTH that are present in the bacterial cells or liberated from the bacterial cells can be performed by a publicly known method. For example, an culture supernatant (extract) of EGT and DTH can be obtained by subjecting the culture to solid-liquid separation such as centrifugation or filtration, whereas an extract thereof in the bacterial cell can be obtained by solvent extraction, hot water extraction, crushing treatment, or the like. From the extract of EGT and DTH or the culture supernatant, EGT can be obtained by subjecting the extract or the culture supernatant to publicly known chromatography such as ion exchange chromatography, hydrophobic chromatography, or gel filtration chromatography.

In the various means for reducing the content of DTH, the preferred content ratio of DTH to EGT is as described above.

The production method may further include a step of adjusting the pH. The numerical range of the optimal pH is as described above.

[Method for Imparting Coloring-Suppressing Effect to Composition Comprising EGT and DTH]

In the present invention, it is also possible to provide a method for imparting a coloring-suppressing effect to a composition comprising EGT and DTH by setting the content of the DTH to 50 parts by mass or less with respect to 100 parts by mass of the EGT. The preferred content ratio of DTH to EGT is as described above.

Examples

Next, a specific description is made of the present invention with reference to Examples and Test Examples, but the present invention is not limited to the following Examples and Test Examples. When there is no particular description, the experiment was performed using the method described in the standard protocol collection related to molecular biology and applied microbiology, or a modified or altered method. Unless otherwise specified, % represents w/v %.

Test Example 1. Stability Evaluation 1 in Composition Comprising EGT and DTH

For compositions comprising L-ergothioneine (EGT) and N,N-dimethyl-L-2-thiohistidine (DTH), the storage stability under various pH conditions was examined as follows.

EGT (manufactured by Tetrahedron) and DTH (manufactured by Tetrahedron) were dissolved in Britton-Robinson Buffers (final concentration: 30 mM) individually having a pH of 3, 4, 5, 6, 7, 8, 9, or 10 such that the final concentration of EGT and DTH, and the pH were as shown in Table 1. In this way, mixed solutions of DTH and EGT were prepared each having a volume of 3.0 ml and having different pH and concentration.

The Britton-Robinson Buffer, which is a wide-range buffer used for adjusting the pH, was prepared as follows. A boric acid+phosphoric acid+acetic acid mixed solution (final concentration: 200 mM each) was fractionated into 20 ml fractions, and the fractions were individually adjusted to pH 3, 4, 5, 6, 7, 8, 9, or 10 with 1 N NaOH, and then diluted to 40 ml with water to yield 300 mM (100 mM each) Britton-Robinson Buffer having pH 3 to 10. Furthermore, 300 mM Britton-Robinson buffer at each pH and water were used for dissolving EGT and DTH such that the final concentration of the Britton-Robinson Buffer was 30 mM. In this way, EGT and DTH mixed solutions in Table 1 were prepared.

Figure 1:
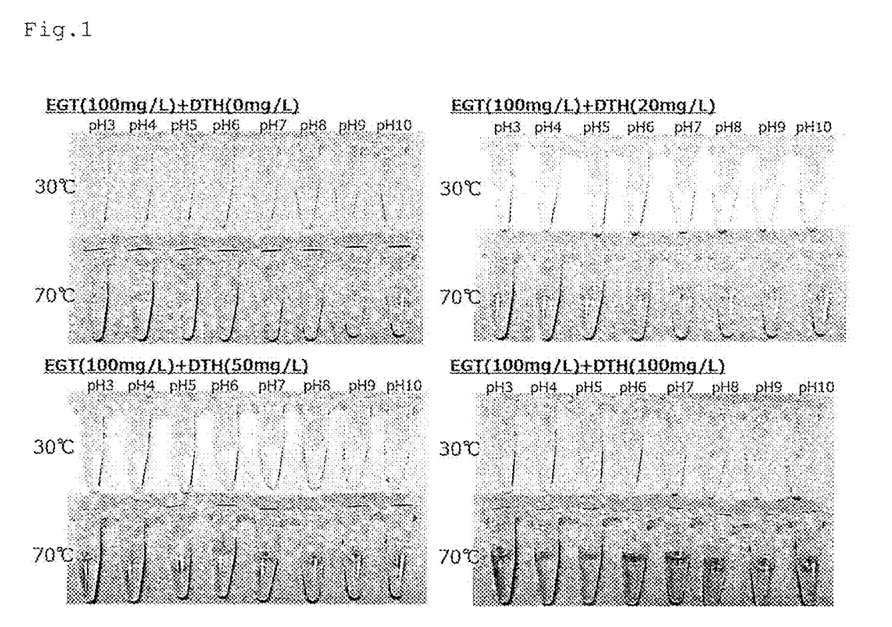
FIG. 1 is a set of graphs showing stability evaluation results of compositions comprising EGT and DTH in Test Example 1.

For each sample number, into two tubes were transferred 1.0 ml of the EGT and DTH mixed solutions described in Table 1, followed by standing at 30° C. or 70° C. for 21 days. Immediately after the start (on Day 0), on Day 8, on Day 14, and on Day 21, a photograph of the tube was taken to record the change in color of the solution, and further 100 µl of the solution was sampled, and then subjected to quantification of EGT and DTH using a high performance liquid chromatography (manufactured by Shimadzu Corporation) under the conditions described in Table 2. FIG. 1 is photographs of the solutions taken on day 14.

As shown in FIG. 1, among the samples stored at 70° C. for 14 days, coloring of the solution from clear and colorless to reddish brown was confirmed in the samples of the test groups of EGT 100 mg/L+DTH 20 mg/L, EGT 100 mg/L+DTH 50 mg/L, and EGT 100 mg/L+DTH 100 mg/L. In addition, the degree of coloring became stronger as the DTH concentration increased. Furthermore, the degree of coloring became stronger as the DTH storage period increased. From the above, a problem that the mixed solution of EGT and DTH was colored was confirmed for the first time in this Test Example.

TABLE 1

| No. | EGT (mg/L) | DTH (mg/L) | pH |
|---|---|---|---|
| 1 | 100 | 0 | 3 |
| 2 | | | 4 |
| 3 | | | 5 |
| 4 | | | 6 |
| 5 | | | 7 |
| 6 | | | 8 |
| 7 | | | 9 |
| 8 | | | 10 |
| 9 | 100 | 20 | 3 |
| 10 | | | 4 |
| 11 | | | 5 |
| 12 | | | 6 |
| 13 | | | 7 |
| 14 | | | 8 |
| 15 | | | 9 |
| 16 | | | 10 |
| 17 | 100 | 50 | 3 |
| 18 | | | 4 |
| 19 | | | 5 |
| 20 | | | 6 |
| 21 | | | 7 |
| 22 | | | 8 |
| 23 | | | 9 |
| 24 | | | 10 |
| 25 | 100 | 100 | 3 |
| 26 | | | 4 |
| 27 | | | 5 |
| 28 | | | 6 |
| 29 | | | 7 |
| 30 | | | 8 |
| 31 | | | 9 |
| 32 | | | 10 |

TABLE 2

| | |
|---|---|
| Instrument used | HPLC Prominence manufactured by Shimadzu Corporation |
| Column | YMC-Pack ODS-AQ (4.6 × 250 mm, particle diameter 5 μm) manufactured by YMC |
| Solvent | 0.1% Formic acid |
| Gradient condition | Isocratic |
| Detection wavelength | 263 nm |
| Flow rate | 0.8 mL/min |
| Column temperature | 30° C. |
| Injection amount | 5 μl |
| Elution time | DTH: around 5.1 min, EGT: around 6.0 min |

Test Example 2. Evaluation 1 of Coloring Suppression in Composition Comprising EGT and DTH As a result of Test Example 1, a novel problem that the mixed solution of EGT and DTH was colored was found. Accordingly, the degree of discoloration was quantified by absorbance measurement, while the concentrations of EGT and DTH were variously examined to search for a method for suppressing coloring.

In the same manner as in Test Example 1, EGT (manufactured by Tetrahedron) and DTH (manufactured by Tetrahedron) were dissolved in a Britton-Robinson Buffer (final concentration: 30 mM) such that the final concentration of EGT and DTH, and the pH were as shown in Tables 3 and 4, and EGT and DTH mixed solutions were prepared each having a volume of 2.0 ml.

Figure 2:
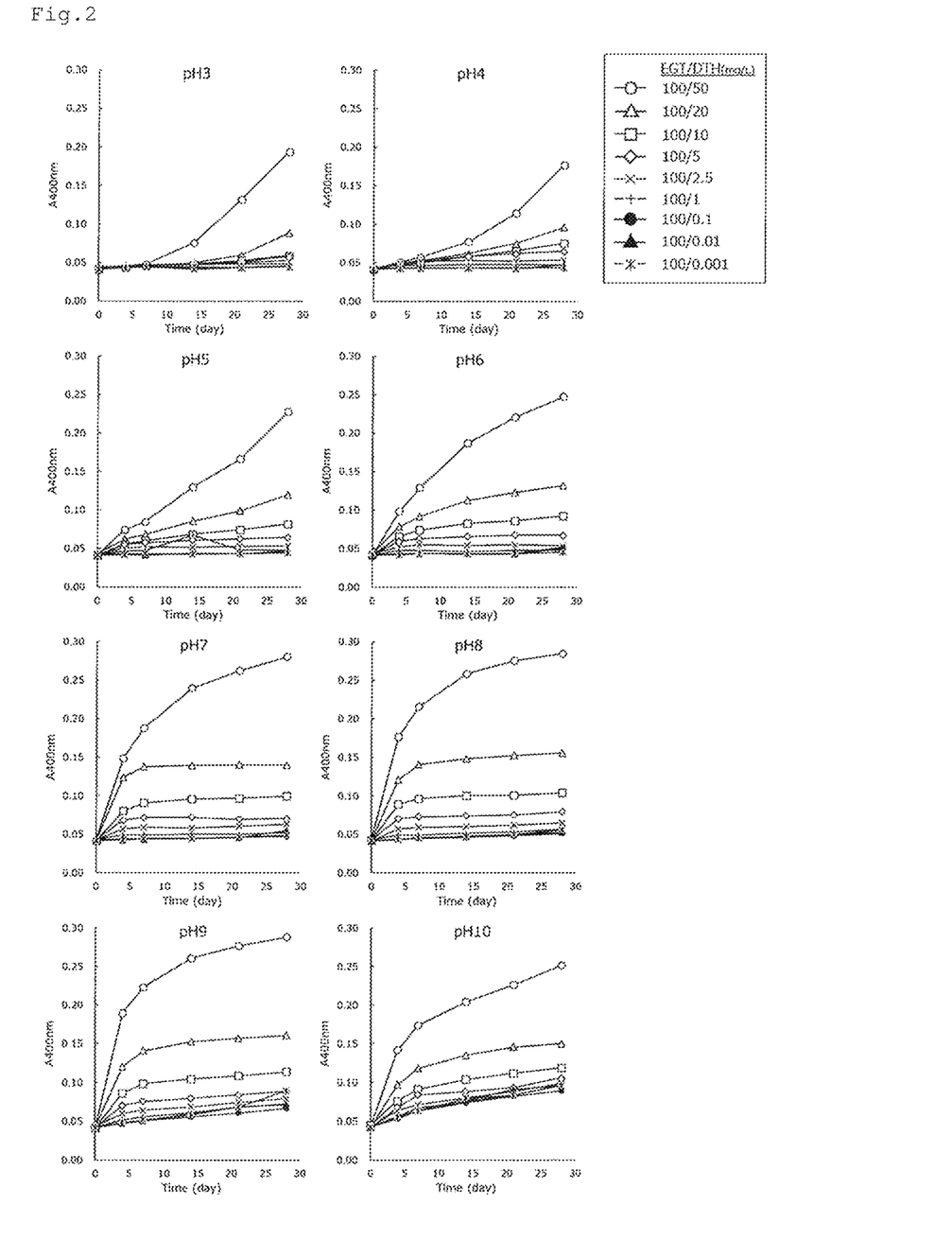
FIG. 2 is a set of graphs showing coloring suppression test results of compositions comprising EGT and DTH in Test Example 2.

Into a 2.0 ml tube, 1.5 ml of each of the EGT and DTH mixed solutions described in Tables 3 and 4 was transferred. Then, 200 μl of mineral oil was overlaid on the liquid surface to prevent evaporation of the solution. The prepared sample was allowed to stand at 70° C. for 28 days, and 200 μl was collected in a 96 well microplate immediately after the start (on day 0), on day 4, on day 7, on day 14, on day 21, and on day 28, to measure the absorbance at 250 to 800 nm using MULTISKAN GO (manufactured by Thermo SCIENTIFIC). FIG. 2 was created using absorbance data at 400 nm among data obtained by absorbance measurement for the samples in Table 3. Furthermore, using 100 μl of the sample after absorbance measurement, quantification of EGT and DTH was performed using a high performance liquid chromatography (manufactured by Shimadzu Corporation) under the conditions shown in Table 2.

TABLE 3

| No. | EGT (mg/L) | DTH (mg/L) | pH |
|---|---|---|---|
| 1 | 100 | 50 | 3 |
| 2 | | 20 | |
| 3 | | 10 | |
| 4 | | 5 | |
| 5 | | 2.5 | |
| 6 | | 1 | |
| 7 | | 0.1 | |
| 8 | | 0.01 | |
| 9 | | 0.001 | |
| 10 | 100 | 50 | 4 |
| 11 | | 20 | |
| 12 | | 10 | |
| 13 | | 5 | |
| 14 | | 2.5 | |
| 15 | | 1 | |
| 16 | | 0.1 | |
| 17 | | 0.01 | |
| 18 | | 0.001 | |
| 19 | 100 | 50 | 5 |
| 20 | | 20 | |
| 21 | | 10 | |
| 22 | | 5 | |
| 23 | | 2.5 | |
| 24 | | 1 | |
| 25 | | 0.1 | |
| 26 | | 0.01 | |
| 27 | | 0.001 | |
| 28 | 100 | 50 | 6 |
| 29 | | 20 | |
| 30 | | 10 | |
| 31 | | 5 | |
| 32 | | 2.5 | |
| 33 | | 1 | |
| 34 | | 0.1 | |
| 35 | | 0.01 | |
| 36 | | 0.001 | |
| 37 | 100 | 50 | 7 |
| 38 | | 20 | |
| 39 | | 10 | |
| 40 | | 5 | |
| 41 | | 2.5 | |
| 42 | | 1 | |

TABLE 3-continued

| No. | EGT (mg/L) | DTH (mg/L) | pH |
|---|---|---|---|
| 43 |  | 0.1 |  |
| 44 |  | 0.01 |  |
| 45 |  | 0.001 |  |
| 46 | 100 | 50 | 8 |
| 47 |  | 20 |  |
| 48 |  | 10 |  |
| 49 |  | 5 |  |
| 50 |  | 2.5 |  |
| 51 |  | 1 |  |
| 52 |  | 0.1 |  |
| 53 |  | 0.01 |  |
| 54 |  | 0.001 |  |
| 55 | 100 | 50 | 9 |
| 56 |  | 20 |  |
| 57 |  | 10 |  |
| 58 |  | 5 |  |
| 59 |  | 2.5 |  |
| 60 |  | 1 |  |
| 61 |  | 0.1 |  |
| 62 |  | 0.01 |  |
| 63 |  | 0.001 |  |
| 64 | 100 | 50 | 10 |
| 65 |  | 20 |  |
| 66 |  | 10 |  |
| 67 |  | 5 |  |
| 68 |  | 2.5 |  |
| 69 |  | 1 |  |
| 70 |  | 0.1 |  |
| 71 |  | 0.01 |  |
| 72 |  | 0.001 |  |

TABLE 4

| No. | EGT (mg/L) | DTH (mg/L) | pH |
|---|---|---|---|
| 1 | 1000 | 500 | 3 |
| 2 |  | 200 |  |
| 3 |  | 100 |  |
| 4 |  | 50 |  |
| 5 |  | 25 |  |
| 6 |  | 10 |  |
| 7 |  | 1 |  |
| 8 |  | 0.1 |  |
| 9 |  | 0.01 |  |
| 10 | 1000 | 500 | 4 |
| 11 |  | 200 |  |
| 12 |  | 100 |  |
| 13 |  | 50 |  |
| 14 |  | 25 |  |
| 15 |  | 10 |  |
| 16 |  | 1 |  |
| 17 |  | 0.1 |  |
| 18 |  | 0.01 |  |
| 19 | 1000 | 500 | 5 |
| 20 |  | 200 |  |
| 21 |  | 100 |  |
| 22 |  | 50 |  |
| 23 |  | 25 |  |
| 24 |  | 10 |  |
| 25 |  | 1 |  |
| 26 |  | 0.1 |  |
| 27 |  | 0.01 |  |
| 28 | 1000 | 500 | 6 |
| 29 |  | 200 |  |
| 30 |  | 100 |  |
| 31 |  | 50 |  |
| 32 |  | 25 |  |
| 33 |  | 10 |  |
| 34 |  | 1 |  |
| 35 |  | 0.1 |  |
| 36 |  | 0.01 |  |
| 37 | 1000 | 500 | 7 |
| 38 |  | 200 |  |
| 39 |  | 100 |  |
| 40 |  | 50 |  |
| 41 |  | 25 |  |
| 42 |  | 10 |  |
| 43 |  | 1 |  |
| 44 |  | 0.1 |  |
| 45 |  | 0.01 |  |
| 46 | 1000 | 500 | 8 |
| 47 |  | 200 |  |
| 48 |  | 100 |  |
| 49 |  | 50 |  |
| 50 |  | 25 |  |
| 51 |  | 10 |  |
| 52 |  | 1 |  |
| 53 |  | 0.1 |  |
| 54 |  | 0.01 |  |
| 55 | 1000 | 500 | 9 |
| 56 |  | 200 |  |
| 57 |  | 100 |  |
| 58 |  | 50 |  |
| 59 |  | 25 |  |
| 60 |  | 10 |  |
| 61 |  | 1 |  |
| 62 |  | 0.1 |  |
| 63 |  | 0.01 |  |
| 64 | 1000 | 500 | 10 |
| 65 |  | 200 |  |
| 66 |  | 100 |  |
| 67 |  | 50 |  |
| 68 |  | 25 |  |
| 69 |  | 10 |  |
| 70 |  | 1 |  |
| 71 |  | 0.1 |  |
| 72 |  | 0.01 |  |

The results of the coloring suppression evaluation test using the samples of Table 3 are shown in FIG. 2. As shown in FIG. 2, for the sample of EGT 100 mg/L+DTH 50 mg/L, the absorbance at 400 nm (A 400 value) representing the degree of coloring increased over time in all pH groups, and the coloring of the EGT and DTH mixed solutions confirmed in Example 1 could be confirmed also from the absorbance. Furthermore, as a result of examined various DTH concentrations, it was confirmed that the A 400 value was lowered by reducing the DTH concentration in all pH groups. Although not limited, it was found that coloring over time was remarkably suppressed particularly when the content ratio of DTH was 20 parts by mass or less with respect to 100 parts by mass of EGT. From the quantitative result of EGT in each sample, it was also shown that decomposition of EGT can be suppressed by reducing the DTH concentration, similarly to coloring.

Figure 3:
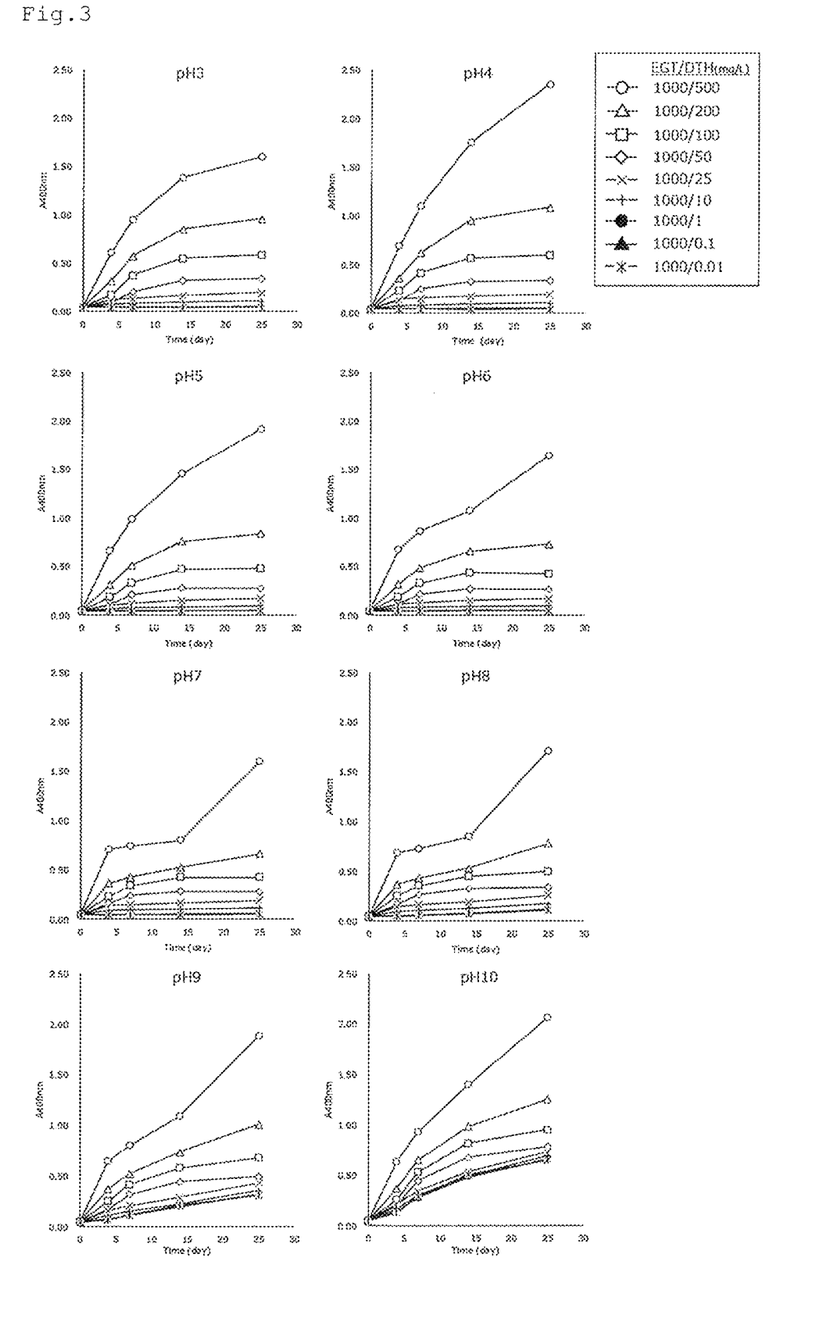
FIG. 3 is a set of graphs showing coloring suppression test results of compositions comprising EGT and DTH in Test Example 2.

In addition, in the coloring suppression evaluation test using the EGT and DTH mixed solutions shown in Table 4, the similar results to those of the samples of Table 3 were obtained. The results are shown in FIG. 3. Specifically, it could be confirmed that the A 400 value was lowered by reducing the DTH concentration in all pH groups, and in particular, it was confirmed that coloring over time could be remarkably suppressed by setting the content ratio of DTH to 20 parts by mass or less with respect to 100 parts by mass of EGT.

Test Example 3. Test for Reducing DTH in EGT Fermentation Method

Microbial EGT production was attempted using *E. coli* expressing the EGT synthetic genes (prior art: WO 2019/

163767 A). As a result of intensive studies, it was accidentally found that the DTH content in the culture solution was significantly reduced by using a strain in which the metJ gene was disrupted. A description is made of this Example below.

From the Nara Institute of Science and Technology, an *E. coli* ΔmetJ strain deficient in a gene encoding metJ prepared from an *E. coli* BW25113 (NBRC103404) strain according to the method described in Mol. Syst. Biol., 2006; 2: 2006.0008 (Baba, T., et al., Construction of *Escherichia coli* K-12 in-frame, single-gene knockout mutants: the Keio collection) was obtained.

The *E. coli* ΔmetJ strain can also be prepared, for example, according to the following method. Construction was performed by a conventionally known method for deleting each gene region of an *E. coli* BW25113 strain by a homologous recombination method using a counter selection vector (including sacB gene or a drug resistance gene) including upstream and downstream sequences of the metJ gene. For the construction of the above-mentioned disrupted strain, reference can be made to M. S. Donnenberg and J. S. Kaper, Infect. Immun., 1991, 4310-4317, H. Mizoguchi et al., Biosci. Biotechnol. Biochem., 2007, 71 (12), 2905-2911, and the like.

As an EGT producing vector, a pACG-EGT (prior art: WO 2019/163767 A) was used. The BW25113 strain and ΔmetJ strain were used, and transformation was performed using the pACG-EGT to yield EGT producing strains (BW25113/pACG-EGT, ΔmetJ/pACG-EGT).

An EGT fermentation production test was performed using the EGT producing strain ΔmetJ/pACG-EGT as constructed above. The BW25113/pACG-EGT obtained by introducing the pACG-EGT into the BW25113 strain was used as a control strain. Each glycerol stock of the BW25113/pACG-EGT and ΔmetJ/pACG-EGT was added to a test tube including tetracycline (final concentration: 10 μg/mL) in 3 mL of LB medium (10 g polypeptone, 5 g yeast extract, 10 g NaCl/1 L medium), followed by shaking culture at 30° C., 200 rpm for 15-18 hours until reaching a stationary phase to yield a preculture solution. Furthermore, the preculture solution was added to 5 mL of 2×YT medium (16 g polypeptone, 10 g yeast extract, 5 g NaCl, 5% Glucose, 5 mM L-Histidine, 2.5 mM L-Cystine, 5 mM L-Methionine, 10 μg/mL tetracycline/1 L culture medium) in a (24 mm test tube so as to have an OD=0.5, followed by main culture with shaking at 30° C., 300 rpm for 96 hours.

Quantification of EGT and DTH was performed as follows. During the main culture, 1 mL of the culture solution was sampled at 24, 48, 72, and 96 hours after the start of the culture to evaluate the culture sample. The bacterial cell turbidity (OD 600) of the sampled culture solution was measured, followed by centrifugation at 14000 rpm for 10 minutes to separate the extracellular culture solution from a precipitate (bacterial cells). The EGT content in the separated extracellular culture solution (extracellular sample) was measured by HPLC. HPLC measurement conditions are as shown in Table 5 below, and quantification was performed based on a peak of EGT occurring around a retention time of 10 minutes and a peak of DTH occurring around a retention time of 8 minutes.

TABLE 5

| | |
|---|---|
| Column | Inertsil HILIC (5 μm; 4.6 φmm × 250 mm) manufactured by GL Sciences Inc. |
| Solvent | 100 mM ammonium acetate/acetonitrile/isopropanol/water (2:82:6:10) |
| Gradient condition | Isocratic |
| Detection wavelength | 265 nm |
| Flow rate | 1 mL/min |
| Column temperature | 40° C. |

Figure 4:
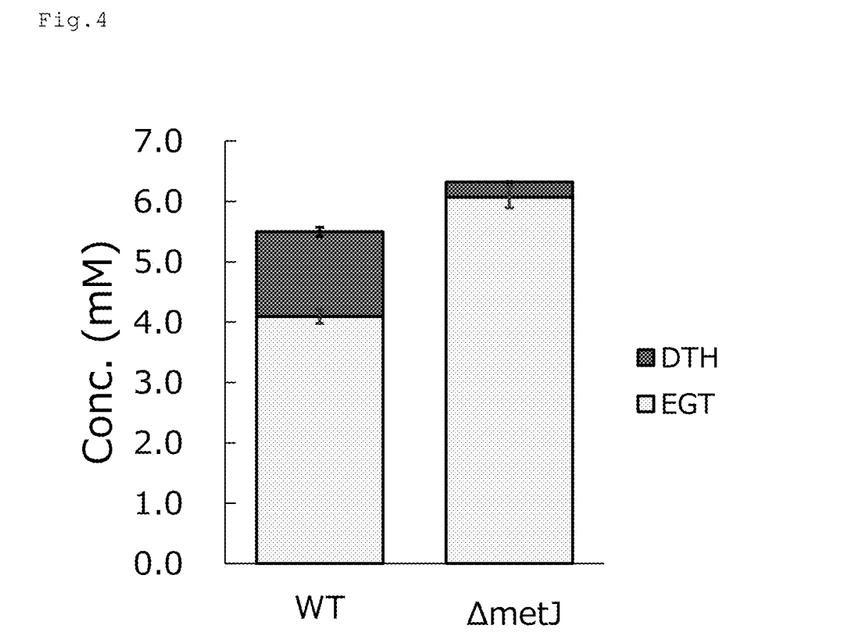
FIG. 4 is a graph showing a result of a test for reducing DTH in an EGT fermentation method in Test Example 3.
Figure 5:
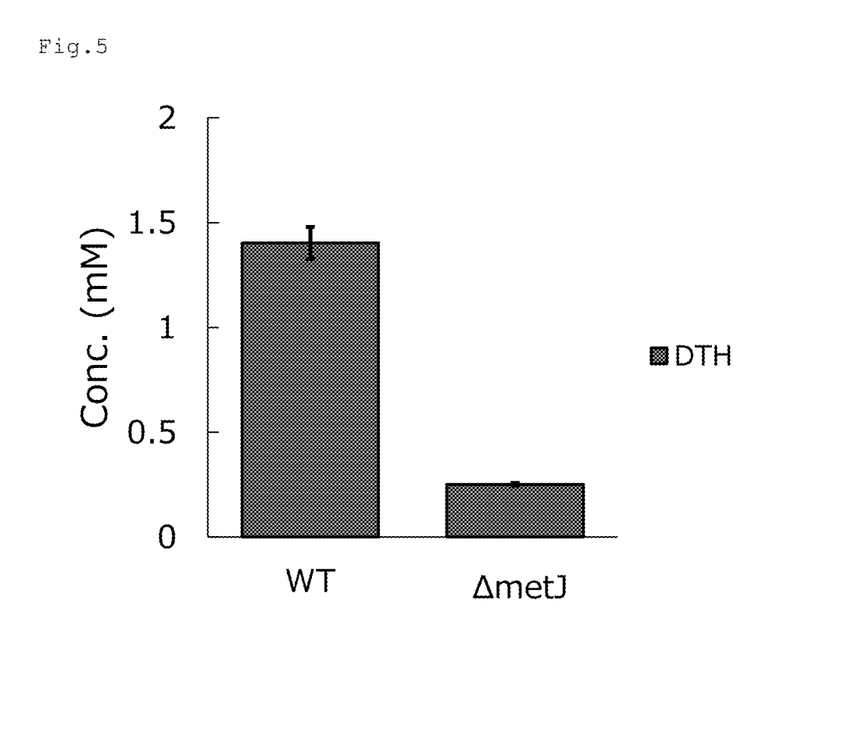
FIG. 5 is a graph showing a result of a test for reducing DTH in an EGT fermentation method in Test Example 3.

As an examination result of the production amounts of EGT and DTH from the cultured WT/pACG-EGT and ΔmetJ/pACG-EGT, as shown in FIGS. 4 and 5, it was found that when the ΔmetJ strain was used, the amount of DTH in the culture solution at 96 hours remarkably decreased to about 1/7 as compared with WT.

The invention claimed is:

1. A composition comprising L-ergothioneine and N,N-dimethyl-L-2-thiohistidine, wherein a content of the N,N-dimethyl-L-2-thiohistidine is reduced.

2. The composition according to claim 1, wherein the content of the N,N-dimethyl-L-2-thiohistidine is reduced so that coloring of the composition is suppressed.

3. The composition according to claim 1, wherein the content of the N,N-dimethyl-L-2-thiohistidine is 50 parts by mass or less with respect to 100 parts by mass of the L-ergothioneine.

4. The composition according to any one of claim 1, wherein the content of the N,N-dimethyl-L-2-thiohistidine is 0.0001 parts by mass or more with respect to 100 parts by mass of the L-ergothioneine.

5. The composition according to any one of claim 1, wherein the content of the N,N-dimethyl-L-2-thiohistidine is 0.05 parts by mass or more with respect to 100 parts by mass of the L-ergothioneine.

6. A composition comprising L-ergothioneine and N,N-dimethyl-L-2-thiohistidine, wherein a content of the N,N-dimethyl-L-2-thiohistidine is 50 parts by mass or less with respect to 100 parts by mass of the L-ergothioneine for suppressing coloring of the composition.

7. A method for producing a composition comprising L-ergothioneine and N,N-dimethyl-L-2-thiohistidine and having suppressed coloring, the method comprising a step of reducing a content of the N,N-dimethyl-L-2-thiohistidine.

8. A method for imparting a coloring-suppressing effect to a composition comprising L-ergothioneine and N,N-dimethyl-L-2-thiohistidine, wherein a content of the N,N-dimethyl-L-2-thiohistidine is 50 parts by mass or less with respect to 100 parts by mass of the L-ergothioneine.

* * * * *

UNITED STATES PATENT AND TRADEMARK OFFICE
CERTIFICATE OF CORRECTION

| | |
|---|---|
| PATENT NO. | : 12,357,614 B2 |
| APPLICATION NO. | : 17/905626 |
| DATED | : July 15, 2025 |
| INVENTOR(S) | : Takeshi Nakatani et al. |

It is certified that error appears in the above-identified patent and that said Letters Patent is hereby corrected as shown below:

On the Title Page

Item (56) In Other Publications, Under Column 2, Line 9, delete "corresponding Tawainese Patent" and insert -- corresponding Taiwanese Patent --.

In the Specification

Under Column 15, Line 44, delete "a (24 mm" and insert -- a Φ 24 mm --.

In the Claims

Under Column 16, Claim 4, Line 34, delete "according to any one of claim" and insert -- according to claim --.

Under Column 16, Claim 5, Line 38, delete "according to any one of claim" and insert -- according to claim --.

Signed and Sealed this
Twenty-third Day of September, 2025

John A. Squires
*Director of the United States Patent and Trademark Office*